(12) United States Patent
Bergh et al.

(10) Patent No.: US 8,466,379 B2
(45) Date of Patent: Jun. 18, 2013

(54) PORTABLE APPARATUS FOR MEASURING EATING RATES AND SATIETY LEVELS

(75) Inventors: Cecilia Bergh, Stockholm (SE); Per Sodersten, Stockholm (SE)

(73) Assignee: Mandometer AB, Huddinge (SE)

( * ) Notice: Subject to any disclaimer, the term of this patent is extended or adjusted under 35 U.S.C. 154(b) by 490 days.

(21) Appl. No.: 12/409,364

(22) Filed: Mar. 23, 2009

(65) Prior Publication Data

US 2010/0236839 A1 Sep. 23, 2010

(30) Foreign Application Priority Data

Mar. 19, 2009 (SE) ...................................... 0900352

(51) Int. Cl.
*G01G 19/414* (2006.01)
*G01G 19/40* (2006.01)
*G01G 19/415* (2006.01)
*A61B 5/00* (2006.01)
*G06F 15/00* (2006.01)

(52) U.S. Cl.
USPC ...................... 177/25.13; 177/25.16; 177/245; 600/300

(58) Field of Classification Search
USPC ......... 177/25.13, 25.16, 25.19, 245; 128/921; 600/300
See application file for complete search history.

(56) References Cited

U.S. PATENT DOCUMENTS

| 5,817,006 | A | * | 10/1998 | Bergh et al. | 600/300 |
|---|---|---|---|---|---|
| 6,478,736 | B1 | * | 11/2002 | Mault | 600/300 |
| 6,485,419 | B2 | * | 11/2002 | Bergh et al. | 600/300 |
| 6,790,178 | B1 | | 9/2004 | Mault et al. | |
| 6,932,766 | B2 | * | 8/2005 | Bergh et al. | 600/300 |
| 2002/0124017 | A1 | * | 9/2002 | Mault | 707/509 |
| 2005/0008993 | A1 | * | 1/2005 | Bergh et al. | 434/127 |
| 2005/0247494 | A1 | * | 11/2005 | Montagnino | 177/60 |
| 2011/0124996 | A1 | * | 5/2011 | Reinke et al. | 600/365 |

OTHER PUBLICATIONS

Westerterp-Plantega et al., "The shape of the cumulative food intake curve in humans, during basic and manipulated meals", Physiology and behavior, US, 1990, v1.47, nr. 3, p. 569-576.

* cited by examiner

*Primary Examiner* — Randy W Gibson
(74) *Attorney, Agent, or Firm* — Fasth Law Offices; Kolf Fasth

(57) ABSTRACT

The invention regards a portable medical apparatus made up of at least two devices (30, 32) adapted to measure eating rate utilized to teach persons to eat according to a predetermined graphic eating curve (10, 24) displayed on a screen and a method therefore. In a specific mode the predetermined graphic curve (24) describes a non linear descending rate of eating behavior. The apparatus comprises a device with cellular capabilities (30), and a scale (32), which devices communicate through near field radiation such as Bluetooth or IR.

20 Claims, 3 Drawing Sheets

PORTABLE APPARATUS FOR MEASURING EATING RATES AND SATIETY LEVELS

PRIOR APPLICATION

This US patent application claims priority from Swedish patent application no. 0900352-6, filed 19 Mar. 2009.

TECHNICAL FIELD

The present invention pertains to a portable medical apparatus made up of at least two devices adapted to measure eating rate utilized to teach persons to eat according to a predetermined graphic eating curve displayed on a screen, and a method therefore.

INCORPORATION

The following documents are hereby incorporated in the following description by reference:

"Decelerated and linear eaters: Effect of eating rate on food intake and satiety Modjtaba Zandian, Ioannis Ioakimidis, Cecilia Bergh, Ulf Brodin, Per Södersten, published by Elsevier, Physiology & Behavior, received Mar. 18, 2008, received in revised form 2 Oct. 2, 2008, and accepted Oct. 9, 2008; and "Linear eaters turned decelerated: Reduction of a risk for disordered eating?" to Modjtaba Zandian, Ioannis Ioakimidis, Cecilia Bergh, Per Södersten, published by Elsevier, Physiology & Behavior, received Jul. 4, 2008, revised Nov. 14, 2008, and accepted Nov. 25, 2008.

BACKGROUND ART

An apparatus named "Mandometer®" has been developed at the Section of Applied Neuroendocrinology and Mandometer® Clinic, Karolinska Institutet, Stockholm, Sweden. It consists of a scale that is connected to a computer. A plate is placed on the scale, the patient puts a measured portion of food determined by a therapist on the plate and the computer records and stores the weight loss from the plate while the patient eats.

The apparatus Mandometer® is patented in several countries for instance in the U.S. under the U.S. Pat. No. 5,817,006 to Bergh et al.

SUMMARY OF THE INVENTION

The present invention has as one aim to provide a portable medical apparatus measuring eating rate utilized to teach persons to eat in a normal eating rate in order to aid them to feel full after an intake of a meal, and still gaining or losing weight in a controlled scientific environment. Another aim is to make possible for those persons to be able to eat at any location that has cellular phone coverage, thereby being able to connect to a remote main computer at any chosen time to record their eating behavior to be evaluated by experts in that field.

Resent scientific studies have shown that a descending rate of eating prevent persons to overeat by eating in a correct manor which has clinical implication for obese to lose weight.

As such the present invention sets forth a portable medical apparatus made up of at least two devices adapted to measure eating rate utilized to teach persons to eat according to a predetermined graphic eating curve displayed on a screen. Thus the present invention comprises:

a first pocket portable device with a screen that stores the predetermined graphic eating curve in a memory, the first device has cellular phone capability and remote near field radiation capabilities for communication with a related second device;

the related second device is a portable scale adapted to communicate with the first device that has cellular phone capability through similar remote near field radiation communication capabilities as the first device;

weighing food on the scale in a measurement session of a length of time, and transmitting the food weight to the first device through the near field radiation when food is removed from the scale by a person eating the food, and through means of software residing in the first device to store the amount of food removed during a session in the memory, displaying the weight of food removed as a measurement point on the screen when it is removed from the scale to make up a real time graphic eating curve to be compared with the predetermined eating curve; and a software means utilized to transmit the stored session through the first device cellular phone capabilities to a remote computer for registration from an arbitrary place, which has cellular coverage for the first device at least at one of a predetermined time, at the will of a person utilizing the medical apparatus, at the finishing of at least one session and at an arbitrary time.

In one embodiment of the invention the scale has a docking station for the first device, whereby at least the screen is visible to a person eating from the scale.

An embodiment comprises that the scale has a docking station for the first device, whereby at least the screen is visible to a person eating from the scale, and wherein the docking station is equipped with a joint/hinge having an adapter to receive the first device with cellular phone capability. The joint/hinge is adapted to move the first device in a predetermined number of degrees around the first device center axes and/or between different elevation levels.

A further embodiment comprises that the joint/hinge is utilized to place the first cellular device in a slot/pocket on the back of the scale when not utilized.

Another embodiment provides that the scale and the first device are integrated into a single device.

A further embodiment provides that the scale has its scale measuring surface formed as a bowl or plate to be served food on.

Still one further embodiment provides that the scale is pocket portable.

One embodiment comprises that the predetermined graphic curve describes a non linear eating behaviour, which is found through science studies to mimic an eating behaviour that is favourable to human beings.

Yet another embodiment comprises that the predetermined graphic curve describes a non linear descending rate of eating behaviour.

A still further embodiment comprises that a predetermined graphic curve of satiety is displayed on the screen, to be compared with satiety ratings made during pre-set time intervals by a person utilizing the apparatus.

Yet a still further embodiment comprises that a predetermined graphic curve of satiety is displayed on the screen, to be compared with satiety ratings made on the screen during pre-set time intervals by a person utilizing the apparatus.

Moreover, the present invention sets forth a portable medical apparatus made up of at least two devices adapted to measure eating rate utilized to teach persons to eat according to a predetermined graphic eating curve displayed on a screen, comprising:

a first pocket portable device with a screen storing the predetermined graphic eating curve in a memory, the first device having cellular phone capability and remote near field radiation capabilities for communication with a related second device;

the predetermined graphic eating curve describing a non linear descending rate of eating behaviour;

the related second device being a portable scale adapted to communicate with the first device having cellular phone capability through similar remote near field radiation communication capabilities as the first device;

weighing food on the scale in a measurement session of a length of time, and transmitting the food weight to the first device through the near field radiation when food is removed from the scale by a person eating the food, and through means of software residing in the first device storing the amount of food removed during a session in the memory, displaying the weight of food removed as a measurement point on the screen when it is removed from the scale to make up a real time graphic eating curve to be compared with the predetermined eating curve.

Furthermore, the present invention also sets forth a method utilizing a portable medical apparatus made up of at least two devices adapted to measure eating rate utilized to teach persons to eat according to a predetermined graphic eating curve displayed on a screen, comprising:

storing the predetermined graphic eating curve in a memory in a first pocket portable device with a screen, the first device having cellular phone capability and remote near field radiation capabilities for communication with a related second device;

describing the predetermined graphic eating curve through a non linear descending rate of eating behaviour;

the related second device being a portable scale adapted to communicate with the first device having cellular phone capability through similar remote near field radiation communication capabilities as the first device;

weighing food on the scale in a measurement session of a length of time, and transmitting the food weight to the first device through the near field radiation when food is removed from the scale by a person eating the food, and through means of software residing in the first device storing the amount of food removed during a session in the memory, displaying the weight of food removed as a measurement point on the screen when it is removed from the scale to make up a real time graphic eating curve to be compared with the predetermined eating curve.

The present invention independent apparatus and method also adheres to the attached dependent claims of the above first mentioned invented apparatus.

BRIEF DESCRIPTION OF THE DRAWINGS

Henceforth reference is had to the attached figures in the accompanying text of the description for a better understanding of the present invention with its embodiments and given examples, wherein.

DETAILED DESCRIPTION OF PREFERRED EMBODIMENTS

Figure 1:
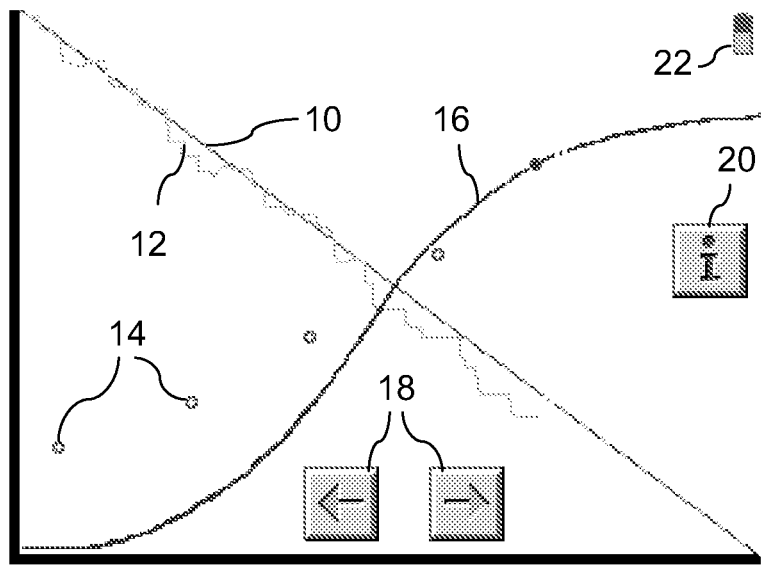
FIG. 1 is illustrating graphics for a linear eating behavior of the present invention.

The present invention is related to a preferably handheld portable medical measuring apparatus consisting of a first device with cellular phone capabilities such as cellular phones, PDA's and like devices that are handheld, and a second device in form of a scale for measuring every portion of food eaten by a person from a plate or bowl or the like placed on the scale during a meal. This apparatus is utilized in teaching persons suffering from anorexia nervosa, bulimia nervosa, obesity, other gastrointestinal problems and persons that would like to have control of their intake of food to keep them fit.

Such a portable device with cellular phone capabilities can be helpful in several situations. It can for instance be utilized by a person to keep arbitrary contact with a therapist for receiving e.g. advices, comfort, and to immediately transmit eating patterns or at least at one of a predetermined time, at the will of a person utilizing the medical apparatus, at the finishing of at least one session and at an arbitrary time. This yields a curve of eating rate which is visible to the patient on the computer screen during a meal and can be compared to a pre-set eating curve on screen. At regular intervals, a rating scale appears on the monitor of the computer and the patient rates her/his level of fullness/satiety. The scale has numerical values from 0 (no satiety) to 100 (maximum satiety). As the patients rate their satiety a dot appears on the screen and yields a curve of the development of satiety (fullness). The patients can thus compare their development of fullness to a "normal" fullness curve again pre-set on screen. During "Mandometer®-training" the patient gradually adopts a more normal pattern of eating and satiety by following the training curves, which are displayed on the monitor during the meal. These methods were originally developed for treating eating disorders such as anorexia and bulimia nervosa: They have been evaluated in a randomized controlled trial with an estimated rate of remission of 75%. It was suggested many years ago that obese people eat at an increased rate and in a pilot study on obese adolescents using Mandometer® this observation was confirmed.

A study regarding obesity among children and youth was conducted at Bristol Royal Hospital for Children in England utilizing the "Mandometer®", which was developed at the Section of Applied Neuroendocrinology and Mandometer® Clinic, Karolinska Institutet, Stockholm, Sweden. It consists of a scale that is connected to a computer. A plate is placed on the scale, the patient puts a measured portion of food determined by a therapist on the plate and the computer records and stores the weight loss from the plate while the patient eats.

This yields a curve of eating rate which is visible to the patient on the computer screen during their meal and can be compared to a pre-set eating curve on screen. At regular intervals, a rating scale appears on the monitor of the computer and the patient rates her/his level of fullness. The scale has for instance numerical values from 0 (no satiety) to 100 (maximum satiety). As the patient rates their satiety a dot appears on the screen and yields a curve of the development of satiety (fullness). The patient can thus compare their development of fullness to a "normal" fullness curve again pre-set on screen. During "Mandometer®-training" the patient gradually adopts a more normal pattern of eating and satiety by following the training curves, which are displayed on the monitor during the meal. These methods were originally developed for treating eating disorders such as anorexia and bulimia nervosa.

This study came to a further improved possible outcome, namely that Mandometer® curves for practicing eating should probably have a decelerated shape, as this pattern may protect individuals for overeating. Analysis of the average speed of eating, as used here, neglects minute-to-minute changes during the meal, which may explain the absence of a statistically significant effect on this simplified measure of speed of eating.

The findings of decelerated eating have been undergoing further scientific tests and analysis emanating in the following scientific papers "Decelerated and linear eaters: Effect of eating rate on food intake and satiety Modjtaba Zandian a, Ioannis Ioakimidis a, Cecilia Bergh a, Ulf Brodin a,b, Per Södersten a, published by Elsevier, Physiology & Behavior, received Mar. 18, 2008, received in revised form 2 Oct. 2, 2008, and accepted Oct. 9, 2008:

a) Karolinska Institutet, Section of Applied Neuroendocrinology, NVS, and Mandometer and Mandolean Clinics, AB Mando, Novum, S-141 57 Huddinge, Sweden b) Karolinska Institutet, LIME, Section of Medical Statistics, S-171 77 Stockholm, Sweden.

Another published paper is "Linear eaters turned decelerated: Reduction of a risk for disordered eating?" to Modjtaba Zandian, Ioannis Ioakimidis, Cecilia Bergh, Per Södersten, published by Elsevier, Physiology & Behavior, received Jul. 4, 2008, revised Nov. 14, 2008, and accepted Nov. 25, 2008.

Henceforth, the apparatus utilized for the descended eating rate scientific findings is described. In FIG. 1 graphics are illustrated for linear eating, which was the standard for measuring eating rate and satiety utilizing the measuring device or the apparatus of the present invention. Hereby, a predetermined linear eating rate curve 10 is depicted together with an actual real time eating curve 12 recorded from a person utilizing the measuring device, or the measuring device of the present invention. The curve 12 should as much as possible match the linear curve 10 to achieve an acceptable normal eating rate, which can aid the person eating to gain or lose weight depending on the persons physical condition.

The dots 14 show how the person eating has rated the satiety during predetermined time periods/intervals, which if connected with a line make up a curve itself illustrating the satiety/fullness of the person eating. Moreover, the FIG. 1 depicts a predetermined sigmoid curve 16 mimicking a normal satiety rating to be compared with the satiety ratings 14 made by the person eating. Buttons 18 are touch buttons utilized to browse between different stored meals in the device with cellular capabilities in accordance with the present invention. Also shown in FIG. 1 is an information button 20, which if pushed for instance shows the amount of food eaten during a session and the duration of the session. Also shown is an icon for the battery charge 22 of the cellular device.

Figure 2:
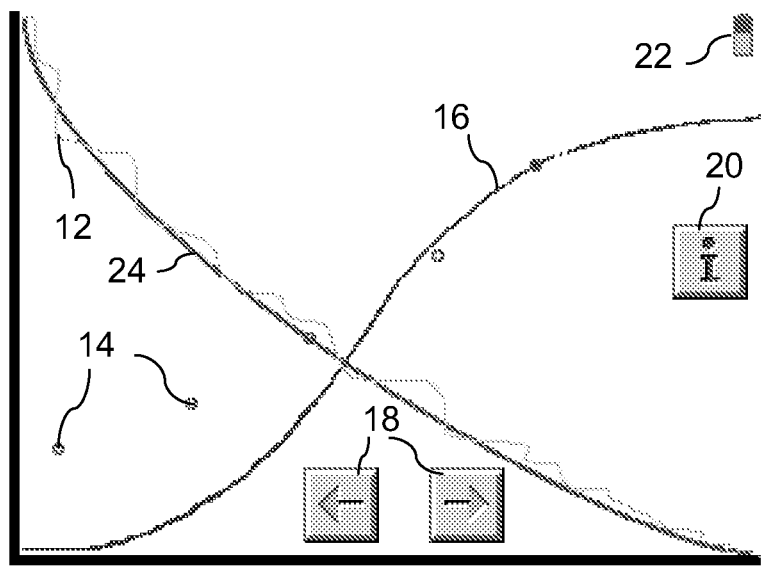
FIG. 2 is illustrating graphics for a descending eating behaviour in accordance with the present invention.

FIG. 2 illustrates similar curves and functions as in FIG. 1, but with the difference that a curve 24 shows a descended eating rate according to recent scientific research results, which better mimics an average persons eating rate.

Figure 3:
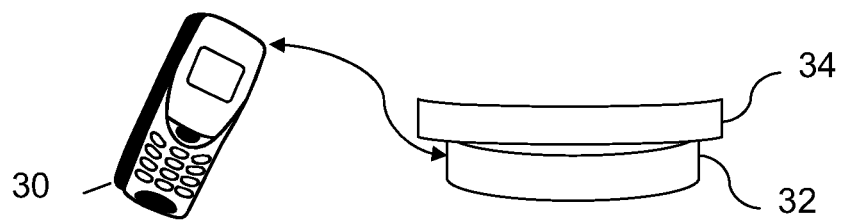
FIG. 3 is schematically illustrating an apparatus with cellular radio capabilities in contact with a scale through near field radiation communication in accordance with the present invention.

FIG. 3 schematically depicts an embodiment of the apparatus according to the present invention by comprising a cellular phone 30 with a display screen of any known constitution such as having a conventional keypad or a touch screen. Moreover the apparatus comprises a scale 32 of preferably a small pocket size. It also shows a plate or bowl 34 utilized to put food on when a person is eating. The cellular device 30 and scale 32 communicate with each other through near field radiation such as for instance Bluetooth or Infrared (IR) or the like, schematically depicted through the double arrow.

A communication between the scale and the cellular device 30 transmits data of how much food the person eating removes from the plate 34 in eating intervals, and the eating rate. The person also rates the satiety 14 in predetermined time intervals on the cellular device screen. Hence, the curves for eating rate 12 and satiety 14 according to FIG. 1 and FIG. 2 are displayed so that a person eating from the plate 34 can adapt its eating rate to the curves 10, 24 for a predetermined eating rate and/or compare its satiety to the curves 16 showing satiety.

Figure 4:
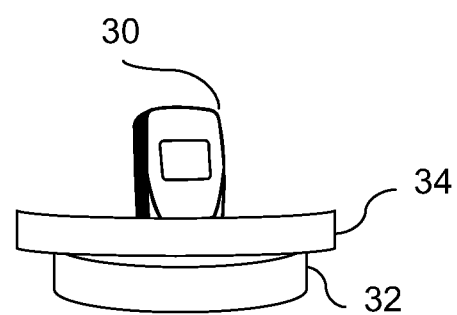
FIG. 4 is schematically illustrating another embodiment of an apparatus with cellular radio capabilities, placed in a docking station of a scale, and in contact with the scale through near field radiation communication in accordance with the present invention.

FIG. 4 schematically shows an embodiment of the present invention where the cellular device 30 is docked in a docking station or integrated with the scale 32, it is also showing a plate or bowl 34.

Figure 5:
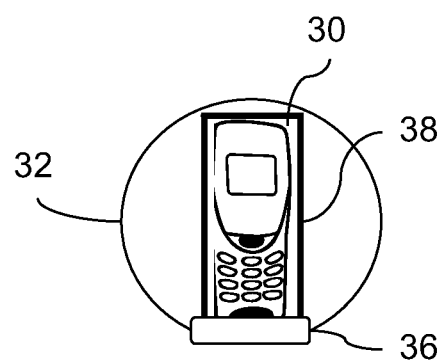
FIG. 5 is schematically illustrating another embodiment of an apparatus with cellular radio capabilities, placed in a docking station of a scale through a joint/hinge, and in contact with the scale through near field radiation communication in accordance with the present invention.

In FIG. 5 it is schematically illustrated an embodiment of a cellular device 30 docked in accordance with FIG. 4 to a scale 32 and folded into a slot 38 in the scale 32 by the aid of a joint/hinge 36. Hereby, the cellular device 30 and the scale form a compact unit when not in use making it easy to keep for instance in a pocket. When in use the cellular device 30 can be folded in at least somewhere between 270 degrees. The docking joint for the cellular device 30 can also be ball like shaped an attached in a ball bearing (not shown), whereby the cellular device can be rotated 360 degrees around its own axes.

The present invention is not restricted to the examples and given embodiments presented above. A person skilled in the art is able to derive further possible embodiments by the attached set of claims.

The invention claimed is:

1. A portable apparatus for measuring eating rates and satiety levels of a user, comprising:

a food device for supporting food disposed thereon;

a scale disposed below the food device, the scale having means for measuring, at predetermined time intervals, a weight of the food disposed on the food device;

a communication device being in communication with the scale and having means for displaying a predetermined continuously descending concave-shaped eating rate curve and a predetermined normal satiety level sigmoid curve;

the communication device having means for displaying, on a display, an amount of the food the user removes from the food device;

the communication device having means for receiving information about satiety levels of the user at the predetermined time intervals; and the communication device having means for simultaneously displaying the measured weight and the amount of food removed by the user from the food device as a continuously descending eating rate and the satiety levels of the user at the predetermined time intervals, the communication device having means for displaying the satiety levels of the user at the predetermined time intervals adjacent to the predetermined normal satiety level sigmoid curve and means for displaying the continuously descending eating rate of the user at the predetermined time intervals adjacent to the predetermined continuously descending concave-shaped eating rate curve.

2. The portable apparatus according to claim 1, wherein the scale has a docking station for the communication device so that the display is visible to the user removing food from the food device.

3. The portable apparatus according to claim 2, wherein the docking station is equipped with a joint/hinge having an adapter to receive the communication device, the joint/hinge having means for moving the communication device in a predetermined number of degrees around a center axis of the communication device and/or between different elevation levels.

4. The portable apparatus according to claim 3, wherein the joint/hinge has a slot/pocket defined therein that is adapted to receive the communication device at a back of the scale.

5. The portable apparatus according to claim 1, wherein the scale and the communication device are integrated into a single device.

6. The portable apparatus according to claim 1, wherein the scale has a scale measuring surface formed as a bowl or plate.

7. The portable apparatus according to claim 1, wherein the scale is pocket portable.

8. The portable apparatus according to claim 1, wherein the predetermined continuously descending concave-shaped eating rate curve mimics an eating behavior that is favorable to human beings.

9. The portable apparatus according to claim 8, wherein the predetermined continuously descending concave-shaped eating rate curve describes an eating behavior.

10. The portable apparatus according to claim 1, wherein the communication device has means for comparing the predetermined normal satiety level sigmoid curve with the satiety levels of the user at the predetermined time intervals.

11. A portable medical apparatus for measuring eating rates and satiety levels of a user, comprising:
a bowl or plate having food disposed thereon;
a scale supporting the bowl or plate, the scale having means for measuring, at predetermined time intervals, a weight of the food disposed on the bowl or plate;
a mobile telephone, having mobile telephone capability, being in communication with the scale and having means for displaying a predetermined continuously descending concave-shaped eating rate curve and a predetermined normal satiety level sigmoid curve retrieved from a memory of the mobile telephone;
the mobile telephone having means for displaying, on a display in real time, an amount of the food the user removes from the bowl or plate at predetermined time intervals;
the mobile telephone having means for receiving information about satiety levels of the user at the predetermined time intervals; and
the mobile telephone having means for simultaneously displaying in real time the measured weight and the amount of food removed by the user from the food device as a continuously descending eating rate and the satiety levels of the user at the predetermined time intervals, the mobile telephone having means for displaying the satiety levels of the user at the predetermined time intervals adjacent to the predetermined normal satiety level sigmoid curve and means for displaying the continuously descending eating rate of the user at the predetermined time intervals adjacent to the predetermined continuously descending concave-shaped eating rate curve.

12. The portable medical apparatus according to claim 11, wherein the mobile telephone has software means for transmitting a stored session to a remote computer for registration from an arbitrary place.

13. The portable medical apparatus according to claim 11, wherein the scale has a docking station for the mobile telephone.

14. The portable medical apparatus according to claim 13 wherein the docking station is equipped with a joint/hinge having an adapter to receive the mobile telephone.

15. The portable medical apparatus according to claim 14, wherein the joint/hinge has a slot/pocket defined therein that is adapted to receive the mobile telephone at a back of the scale.

16. The portable medical apparatus according to claim 11, wherein the scale and the mobile telephone are integrated into a single device.

17. The portable medical apparatus according to claim 11, wherein the scale has a scale measuring surface formed as a bowl or plate.

18. The portable medical apparatus according to claim 11, wherein the scale is pocket portable.

19. A method for using an apparatus, comprising:
providing a scale supporting a food device having food disposed thereon and a communication device being in communication with the scale;
measuring, at predetermined time intervals, a weight of the food disposed on the food device;
displaying a predetermined continuously descending concave-shaped eating rate curve and a predetermined normal satiety level sigmoid curve on a display;
removing an amount of food from the food device;
receiving information about satiety levels of the user at the predetermined time intervals; and
simultaneously displaying in real time a measured weight and the amount of food removed from the food device as a continuously descending eating rate and the satiety levels of the user at the predetermined time intervals;
displaying the satiety levels of the user at the predetermined time intervals adjacent to the predetermined normal satiety level sigmoid curve; and
displaying the continuously descending eating rate of the user at the predetermined time intervals adjacent to the predetermined continuously descending concave-shaped eating rate curve.

20. The method according to claim 19, wherein the method further comprises transmitting a stored session to a remote computer for registration from an arbitrary place.

* * * * *